US00PP15277P2

(12) United States Plant Patent
Dodd, Jr.

(10) Patent No.: US PP15,277 P2
(45) Date of Patent: Oct. 26, 2004

(54) ***LOROPETALUM* PLANT NAMED 'BILL WALLACE'**

(50) Latin Name: *Loropetalum chinensis*
Varietal Denomination: Bill Wallace

(75) Inventor: Thomas Henry Dodd, Jr., Semmes, AL (US)

(73) Assignee: Carolina Nurseries, Inc., Moncks Corner, SC (US)

( * ) Notice: Subject to any disclaimer, the term of this patent is extended or adjusted under 35 U.S.C. 154(b) by 0 days.

(21) Appl. No.: 10/743,108

(22) Filed: Dec. 22, 2003

(51) Int. Cl.[7] ..... A01H 5/00
(52) U.S. Cl. ..... Plt./226
(58) Field of Search ..... Plt./226

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Loropetalum* plant named 'Bill Wallace', characterized by its outwardly spreading and procumbent plant habit; short internodes; dense and bushy growth habit; relatively small leaves; and dark reddish green-colored leaves.

1 Drawing Sheet

Botanical classification/cultivar designation: *Loropetalum chinensis* cultivar Bill Wallace.

BACKGROUND OF THE INVENTION

The present Invention relates to a new and distinct cultivar of *Loropetalum* plant, botanically known as *Loropetalum chinensis*, and hereinafter referred to by the name 'Bill Wallace'.

The new *Loropetalum* is a naturally-occurring branch mutation of the *Loropetalum chinensis* cultivar Burgundy, not patented. The new *Loropetalum* was discovered and selected by the Inventor from within a large population of plants of the cultivar Burgundy in a controlled environment in Semmes, Ala. in 1996.

Asexual reproduction of the new cultivar by cuttings at Semmes, Ala., since July, 1999, has shown that the unique features of this new *Loropetalum* are stable and reproduced true to type in successive generations of asexual reproduction.

SUMMARY OF THE INVENTION

The following traits have been repeatedly observed and are determined to be the unique characteristics of 'Bill Wallace'. These characteristics in combination distinguish 'Bill Wallace' as a new and distinct cultivar:

1. Outwardly spreading and procumbent plant habit.
2. Short internodes, dense and bushy growth habit.
3. Relatively small leaves.
4. Dark reddish green-colored leaves.

In side-by-side comparisons conducted in Moncks Corner, S.C., plants of the new *Loropetalum* differed from plants of the cultivar Burgundy in the following characteristics:

1. Plants of the new *Loropetalum* were outwardly spreading and procumbent in habit whereas plants of the cultivar Burgundy were much taller and upright.
2. Plants of the new *Loropetalum* had shorter internodes and were denser and bushier than plants of the cultivar Burgundy.

The new *Loropetalum* can be compared to the cultivar, Zhuzhou Fuchsia, not patented. However, in side-by-side comparisons conducted in Moncks Corner, S.C., plants of the new *Loropetalum* differed from plants of the cultivar Zhuzhou Fuchsia in the following characteristics:

1. Plants of the new *Loropetalum* were outwardly spreading and procumbent in habit whereas plants of the cultivar Zhuzhou Fuchsia were much taller and upright.
2. Plants of the new *Loropetalum* had shorter internodes and were denser and bushier than plants of the cultivar Zhuzhou Fuchsia.
3. Plants of the new *Loropetalum* had smaller and narrower leaves than plants of the cultivar Zhuzhou Fuchsia.
4. Plants of the new *Loropetalum* had reddish green-colored leaves whereas plants of the cultivar Zhuzhou Fuchsia had dark purple-colored leaves.

The new *Loropetalum* can also be compared to the cultivar, Ruby, not patented. However, in side-by-side comparisons conducted in Moncks Corner, S.C., plants of the new *Loropetalum* differed from plants of the cultivar Ruby in the following characteristics:

1. Plants of the new *Loropetalum* were outwardly spreading and procumbent in habit whereas plants of the cultivar Ruby were taller and upright.
2. Plants of the new *Loropetalum* had shorter internodes and were denser and bushier than plants of the cultivar Ruby.
3. Plants of the new *Loropetalum* had smaller and narrower leaves than plants of the cultivar Ruby.

BRIEF DESCRIPTION OF THE PHOTOGRAPHS

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Loropetalum*. The photograph comprises a side perspective view of a typical plant of 'Bill Wallace' grown in a container.

DETAILED BOTANICAL DESCRIPTION

In the following description, color references are made to The Royal Horticultural Society Colour Chart, 1995 Edition, except where general terms of ordinary dictionary significance are used. Plants grown in three-gallon containers were used for the aforementioned photograph and following description. Plants were about three years from planting rooted cuttings. Plants were grown under conditions which closely approximate commercial production conditions during the summer in Moncks Corner, S.C. in an outdoor nursery. During the production period, day temperatures ranged from about 28 to 35° C. and night temperatures ranged from about 24 to 28° C.

Botanical classification: *Loropetalum chinensis* cultivar Bill Wallace.

Parentage: Naturally-occurring branch mutation of *Loropetalum chinensis* cultivar Burgundy, not patented.

Propagation:

*Type cutting.*—Vegetative cuttings.

*Time to initiate roots, summer.*—About 15 days at 29° C.

*Time to initiate roots, winter.*—About 35 days at 18° C.

*Time to produce a rooted young plant, summer.*—About six months at 29° C.

*Time to produce a rooted young plant, winter.*—About eight months at 18° C.

*Root description.*—Freely branching; dark red in color.

Plant description:

*General appearance.*—Outwardly spreading and procumbent plant habit.

*Growth and branching habit.*—Freely branching. Pinching, that is, removal of the terminal apices, enhances branching with lateral branches potentially forming at every node. Moderately vigorous growth habit; moderate growth rate.

*Plant height.*—About 23 cm.

*Plant diameter or spread.*—About 63 cm.

*Lateral branch description.*—Length: About 27 cm. Diameter: About 2.5 mm. Internode length: About 1.8 cm. Texture: Young stems, pubescent and scaly; older stems, woody. Color: Young stems, close to 175A; older stems, close to 200D.

*Foliage description.*—Arrangement: Alternate, simple. Length: About 2.8 cm. Width: About 1.5 cm. Shape: Elliptical. Apex: Acute. Base: Narrowly oblique. Margin: Entire. Texture, upper and lower surfaces: Pubescent; coarse. Venation pattern: Pinnate. Color: Developing and fully expanded foliage, upper surface: Much darker green than 147A overlain with close to 187A; venation, similar to lamina. Developing and fully expanded foliage, lower surface: Slightly lighter than 189A underlain with close to 187A; venation, close to 186A. Petiole: Length: About 4 mm. Diameter: About 1 mm. Texture, upper and lower surfaces: Pubescent. Color, upper and lower surfaces: 146A.

Flower description: Flower development has not been observed on plants to date.

Disease/pest resistance: Plants of the new *Loropetalum* have not been observed to be resistant to pathogens and pests common to *Loropetalum*.

Weather tolerance: Plants of the new *Loropetalum* have been observed to be tolerant to wind, rain and temperatures ranging from −10 to 39° C.

It is claimed:

1. A new and distinct cultivar of *Loropetalum* plant named 'Bill Wallace', as illustrated and described.

* * * * *

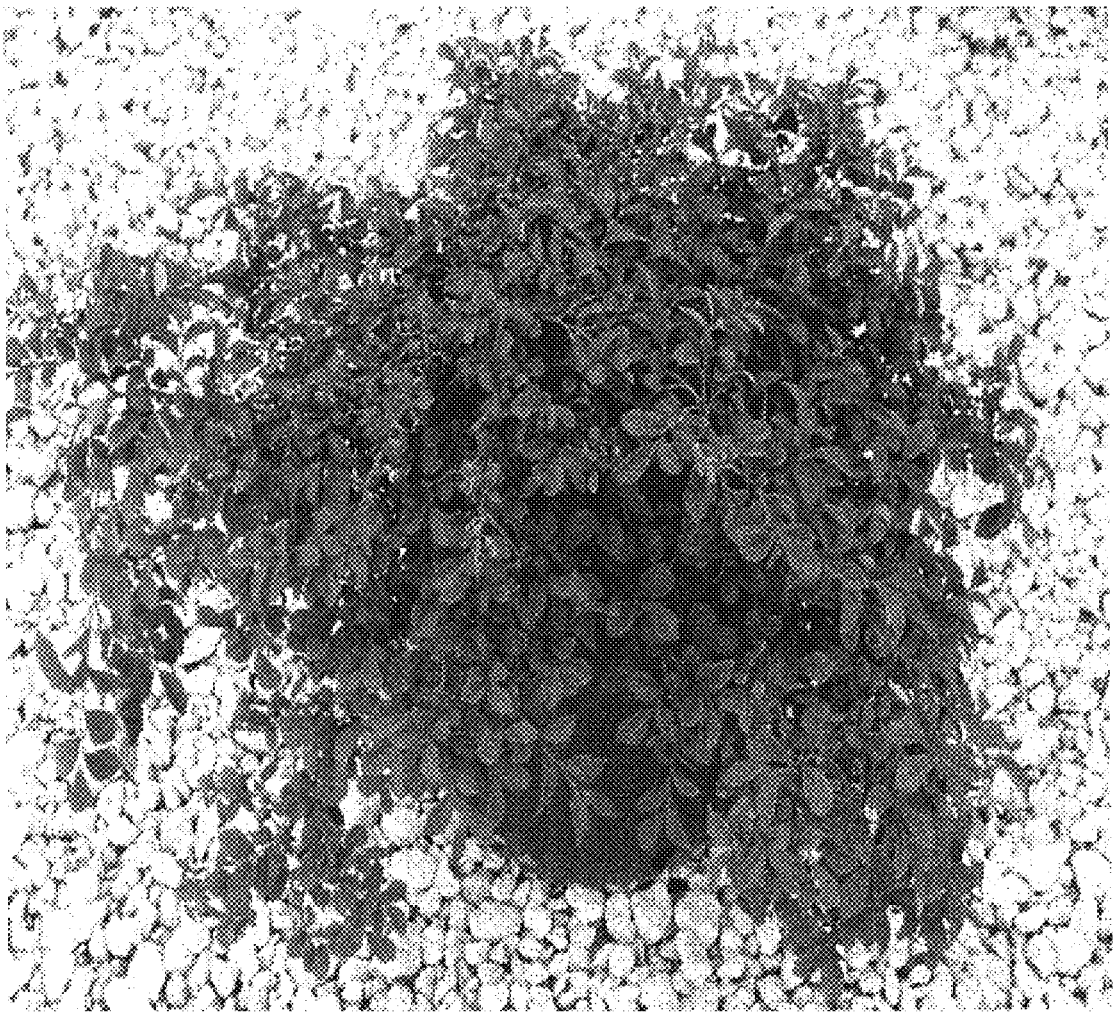

UNITED STATES PATENT AND TRADEMARK OFFICE

CERTIFICATE OF CORRECTION

PATENT NO. : PP 15,277 P2
APPLICATION NO. : 10/743108
DATED : October 26, 2004
INVENTOR(S) : Thomas Henry Dodd, Jr.

It is certified that error appears in the above-identified patent and that said Letters Patent is hereby corrected as shown below:

On the title page:

Item (54), **"*LOROPETALUM* PLANT NAMED 'BILL WALLACE'"**

Should read **--*LOROPETALUM* PLANT NAMED 'CN1 TWO'--**

Item (50), "Latin Name: *Loropetalum chinensis*
Varietal Denomination: Bill Wallace"

Should read --Latin Name: *Loropetalum chinensis*
Varietal Denomination: CN1 TWO--

Item (57), "ABSTRACT

A new and distinct cultivar of *Loropetalum* plant named 'Bill Wallace', characterized by its outwardly spreading and procumbent plant habit; short internodes; dense and bushy growth habit; relatively small leaves; and dark reddish green-colored leaves."

Should read --ABSTRACT

A new and distinct cultivar of *Loropetalum* plant named 'CN1 TWO', characterized by its outwardly spreading and procumbent plant habit; short internodes; dense and bushy growth habit; relatively small leaves; and dark reddish green-colored leaves.--

Column 1,
Line 2, "Bill Wallace" should read --CN1 TWO--;
Line 8, "Bill Wallace" should read --CN1 TWO--;
Line 25, "Bill Wallace" should read --CN1 TWO--;
Line 27, "Bill Wallace" should read --CN1 TWO--;

Column 2,
Line 43, "Bill Wallace" should read --CN1 TWO--;

Column 3,
Line 16, "Bill Wallace" should read --CN1 TWO--; and

UNITED STATES PATENT AND TRADEMARK OFFICE

CERTIFICATE OF CORRECTION

PATENT NO. : PP 15,277 P2
APPLICATION NO. : 10/743108
DATED : October 26, 2004
INVENTOR(S) : Thomas Henry Dodd, Jr.

It is certified that error appears in the above-identified patent and that said Letters Patent is hereby corrected as shown below:

Column 4,
Line 34, "Bill Wallace" should read --CN1 TWO--.

Signed and Sealed this

Twentieth Day of February, 2007

JON W. DUDAS
*Director of the United States Patent and Trademark Office*